: US005688280A

United States Patent [19]
Booth, Jr. et al.

[11] Patent Number: 5,688,280
[45] Date of Patent: Nov. 18, 1997

[54] INSTRUMENTATION FOR USE IN ORTHOPAEDIC SURGERY

[75] Inventors: Robert E. Booth, Jr., Philadelphia, Pa.; Gregory C. Stalcup, Columbia City, Ind.; Rodney Bays, Pierceton, Ind.; Billy N. Sisk, Claypool, Ind.; Steven E. Dietzel, Peru, Ind.; Timothy R. Miller, Austin, Tex.

[73] Assignee: Bristol-Myers Squibb Co., New York, N.Y.

[21] Appl. No.: 686,894

[22] Filed: Jul. 26, 1996

Related U.S. Application Data

[63] Continuation-in-part of Ser. No. 369,226, Jan. 6, 1995, Pat. No. 5,540,696.

[51] Int. Cl.⁶ ............................................. A61B 17/15
[52] U.S. Cl. ........................................ 606/88; 606/102
[58] Field of Search ............................ 606/86, 87, 88, 606/90, 102, 105

[56] References Cited

U.S. PATENT DOCUMENTS

| | | | |
|---|---|---|---|
| 4,487,203 | 12/1984 | Androphy | 128/303 R |
| 4,501,266 | 2/1985 | McDaniel | 128/69 |
| 4,566,448 | 1/1986 | Rohr, Jr. | 128/92 H |
| 4,567,886 | 2/1986 | Petersen | 128/92 H |
| 4,574,794 | 3/1986 | Cooke et al. | 128/92 H |
| 4,655,197 | 4/1987 | Atkinson | 128/66 |
| 4,703,751 | 11/1987 | Pohl | 128/92 |
| 4,907,578 | 3/1990 | Petersen | 606/79 |
| 4,938,762 | 7/1990 | Wehrli | 606/88 |
| 5,059,194 | 10/1991 | Michelson | 606/61 |
| 5,116,338 | 5/1992 | Poggie et al. | 606/90 |
| 5,213,112 | 5/1993 | Niwa et al. | 128/774 |
| 5,282,803 | 2/1994 | Lackey | 606/80 |
| 5,342,367 | 8/1994 | Ferrante et al. | 606/86 |
| 5,342,368 | 8/1994 | Petersen | 606/88 |
| 5,344,423 | 9/1994 | Dietz et al. | 606/87 |
| 5,364,401 | 11/1994 | Ferrante et al. | 606/84 |
| 5,417,695 | 5/1995 | Axelson, Jr. | 606/89 |
| 5,454,816 | 10/1995 | Ashby | 606/88 |
| 5,468,244 | 11/1995 | Attfield et al. | 606/90 |

FOREIGN PATENT DOCUMENTS

| | | |
|---|---|---|
| 0 682 916 A3 | 5/1996 | European Pat. Off. |
| 2648699 | 12/1990 | France . |
| 2 261 604A | 5/1993 | United Kingdom . |
| WO 94/00056 | 1/1994 | WIPO . |
| WO 94/05212 | 3/1994 | WIPO . |

OTHER PUBLICATIONS

AOR Knee Instrumentation, Thomas Petersen, M.D., Jo Miller, M.D., Jorge O. Galante, M.D. (Zimmer, Inc.).
New Jersey LCS Total Knee System, Frederick K. Buechel, M.D. (DePuy).

*Primary Examiner*—Michael Buiz
*Assistant Examiner*—David O. Reip
*Attorney, Agent, or Firm*—Todd A. Dawson

[57] ABSTRACT

The instrumentation set of this invention assists the surgeon in selecting the proper implant components, in determining the amount of distal bone to resect, and in aligning instrumentation designed to resect the bone. The instrumentation set provides numerous systems for verifying to the surgeon that he has correctly aligned the instruments prior to removing any bone. The set includes a rotational alignment guide, which aids the surgeon in establishing the appropriate rotational alignment for the knee as determined by reference to standard femoral landmarks such as the posterior condyles and epicondyles. The rotational alignment guide includes a slot for guiding a saw blade for removal of the posterior condyles of the femur. The set further includes a tensor designed to tense the knee joint in flexion and extension. The tensor is activated by a torque wrench so that a measured mount of tension force can be applied to the joint. The tensor is configured to slidably carry a sizing rod which contacts the femur and includes a plurality of markings, which relate to the size of the femur as well as the spacing between the femur and tibia. This information is used by the surgeon to select the proper size of femoral and tibial articulate surface components. The sizing rod also indicates to the surgeon any variation required in the amount of bone to be resected.

5 Claims, 9 Drawing Sheets

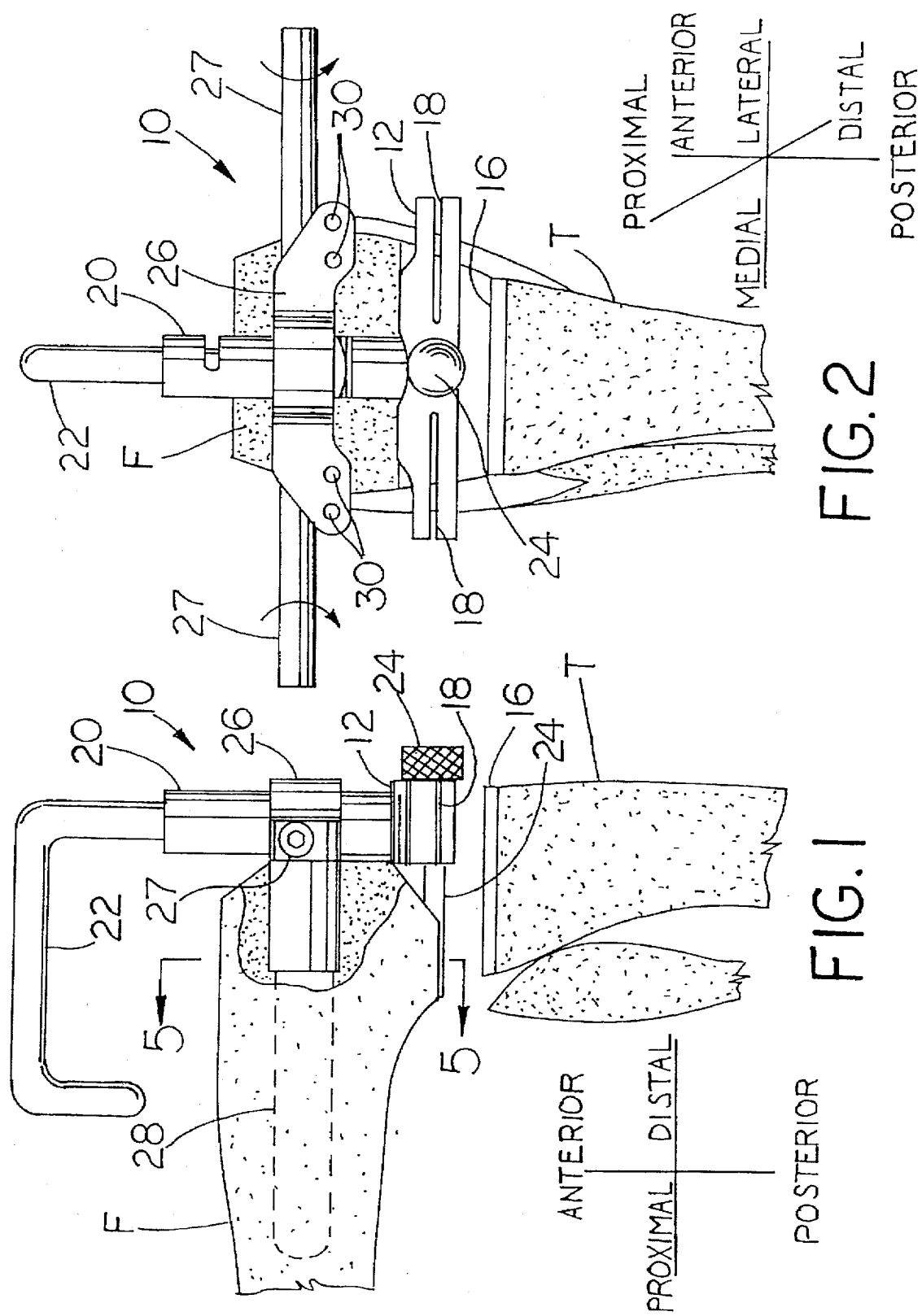

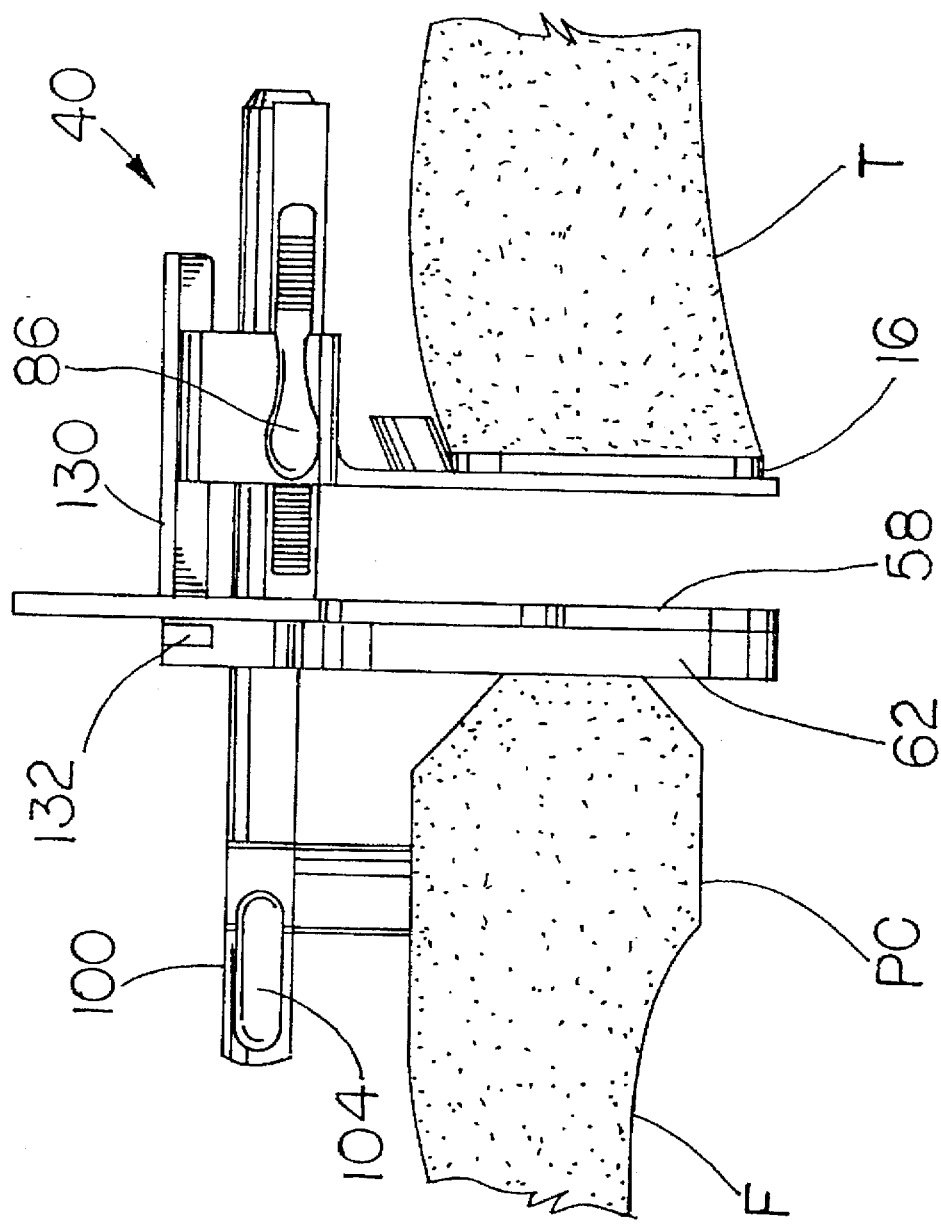

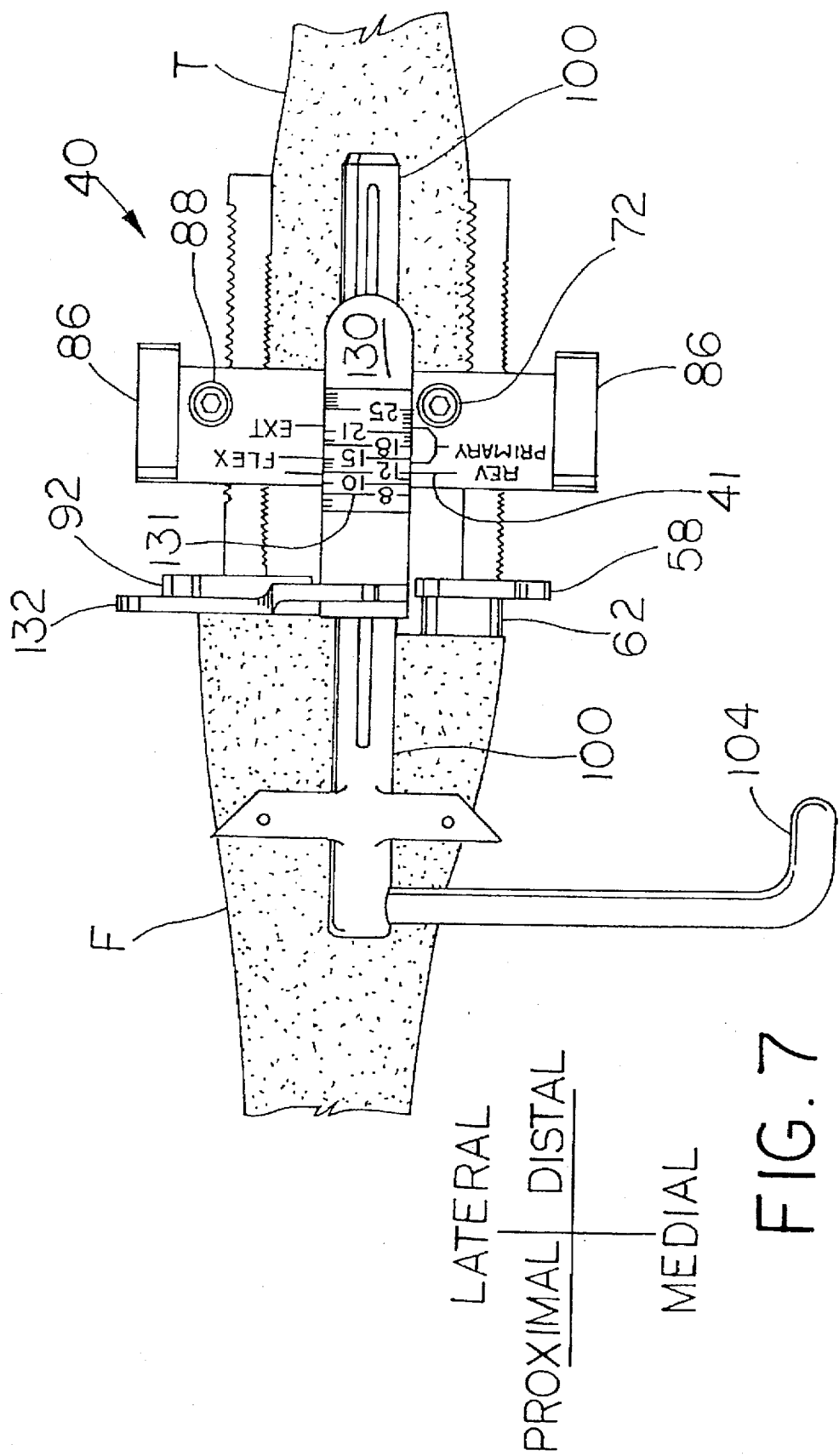

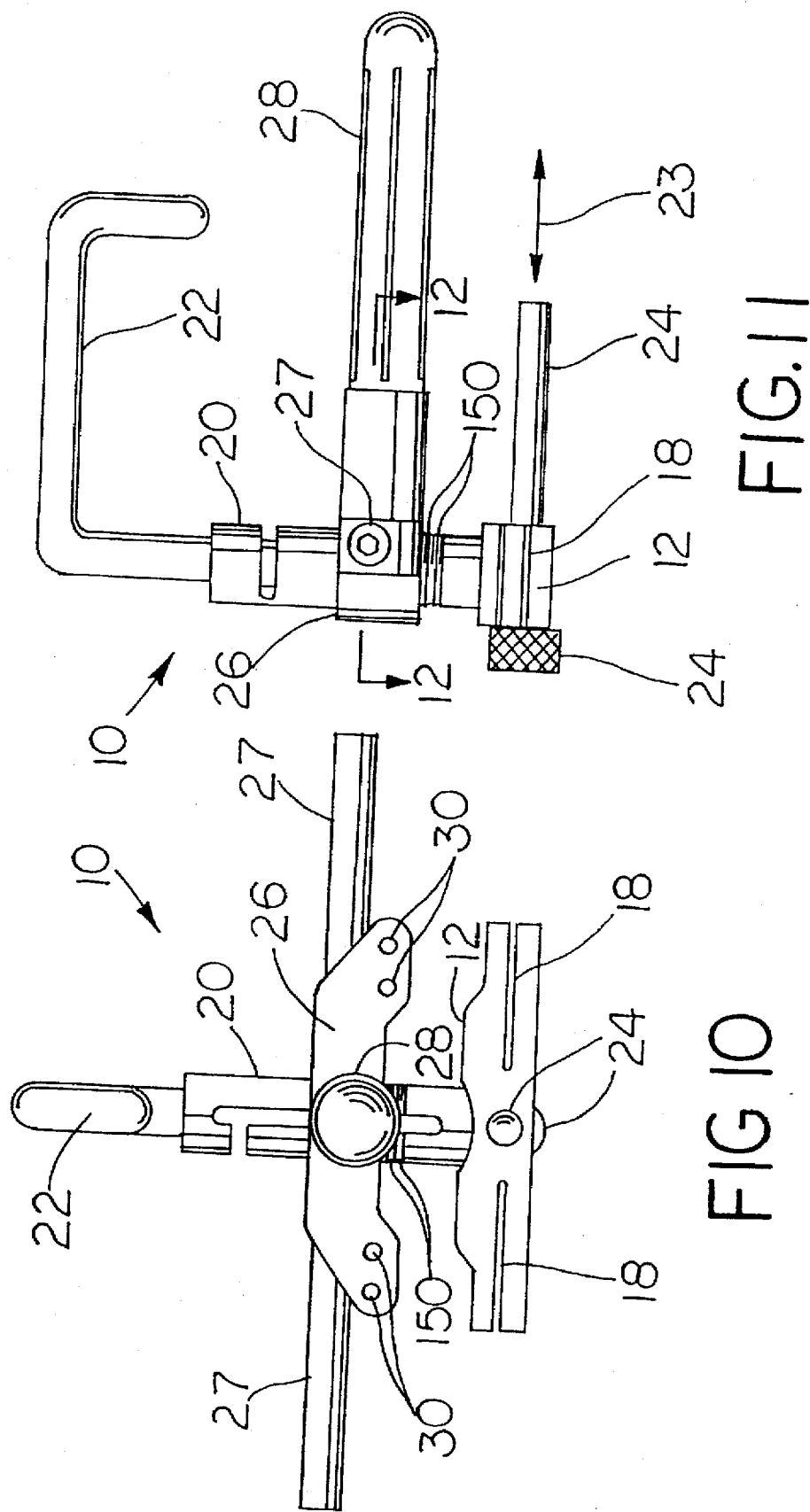

INSTRUMENTATION FOR USE IN ORTHOPAEDIC SURGERY

CROSS REFERENCE TO RELATED APPLICATIONS

This is a continuation-in-part of U.S. patent application Ser. No. 08/369,226, filed Jan. 6, 1995, now U.S. Pat. No. 5,540,696, entitled "INSTRUMENTATION FOR USE IN ORTHOPAEDIC SURGERY."

FIELD OF THE INVENTION

This invention relates to instrumentation used in orthopaedic surgery during a revision total knee replacement procedure for sizing the femur and polyethylene components as well as providing indications of proper alignment and assisting the surgeon in providing the proper soft tissue balance for the joint.

BACKGROUND OF THE INVENTION

In a primary total knee arthroplasty procedure to replace a worn or damaged knee, the orthopaedic surgeon spends a good deal of time ensuring the resulting knee joint will be balanced. A balanced knee joint will demonstrate proper ligament tension through the joint's range of motion as well as a predetermined angle between the mechanical axis of the knee and the anatomical axis of the knee. This provides for a more natural acting joint prosthesis and improves the wear characteristics of the prosthesis. Selecting the proper size of prosthetic components is also an important factor which affects the success of the procedure. If the wrong components are selected, the tendons could be too tight or too loose resulting in poor performance for the knee.

In a revision knee surgery, a surgeon removes existing orthopaedic implants from the distal femur and proximal tibia and replaces the same with new implants. Typically, the distal femur and tibia includes one or more defects which may have led to the failure of the primary implant. Therefore, after removal of the original implants from the knee joint, the previously resected distal femur and proximal tibia may need to be re-cut or re-shaped to properly interfit and mate with the associated new implant. Similar to a primary surgery, an orthopaedic surgeon in a revision surgery also spends a good deal of time ensuring the resulting knee joint will be balanced, and ensuring that proper size prosthetic components are selected.

What is needed in the art is orthopaedic instrumentation which may be used in a revision knee surgery to properly balance the knee joint and size the prosthetic components.

SUMMARY OF THE INVENTION

The instrumentation set of this invention assists the surgeon in selecting the proper size of implant components including any augments that may be needed, in determining the mount of distal bone to resect, in providing the proper soft tissue balance, and in aligning instrumentation designed to resect the bone.

The instrumentation set provides for numerous systems for verifying to the surgeon that he has correctly aligned the instruments and balanced the joint prior to resecting the femur. The set includes a rotational alignment guide, which aids the surgeon in establishing the appropriate rotational alignment for the knee as determined by reference to standard femoral landmarks such as the posterior condyles and epicondyles. The rotational alignment guide includes a slot for guiding a saw blade for resection of the posterior condyles of the femur.

The set further includes a tensor designed to tense the knee joint in flexion and extension. The tensor is activated by a torque wrench so that a measured amount of tension force can be applied to the joint. The tensor is configured to slidably carry sizing rods which contact the femur and include a plurality of markings relating to the size of the femur as well as the spacing between the femur and tibia. This information is used by the surgeon to select the proper size of femoral and tibial articulate surface components. The sizing rods are connected to the tensor when the knee joint is in flexion and in extension which will indicate to the surgeon any variation required in the amount of bone to be resected and the femoral component size.

Accordingly, it is an advantage of this invention to provide for a novel set of instruments for tensioning and sizing the knee joint in a revision procedure.

Another advantage of the invention is to provide a novel tensioning device wherein the knee joint may be placed in tension in a flexed and/or extended position during a knee joint revision procedure.

Another advantage of the invention is to provide a novel system for measuring the knee joint, including instruments for measuring the gap between the tibia and femur as well as measuring the size of the femur.

Yet another advantage of the invention is to provide for a set of instruments that determine the amount of bone to be resected relative to a standard resection.

Still other advantages of the invention will become apparent upon a reading of the following description taken with the accompanying drawings.

BRIEF DESCRIPTION OF THE DRAWINGS

FIGS. 1 is a side view of an embodiment of a rotational alignment guide of the present invention;

FIG. 2 is an end view of the rotational alignment guide shown in FIG. 1;

FIG. 6 is a side view of the tensor shown in FIGS. 3 and 4, with the knee joint in an extension position;

FIG. 7 is a top view of the tensor shown in FIG. 6;

FIG. 10 is an end elevational view of the rotational alignment guide shown in FIG. 10;

FIG. 11 is a side elevational view of the rotational alignment guide shown in FIGS. 9 and 10.

DETAILED DESCRIPTION OF THE INVENTION

Figure 3:
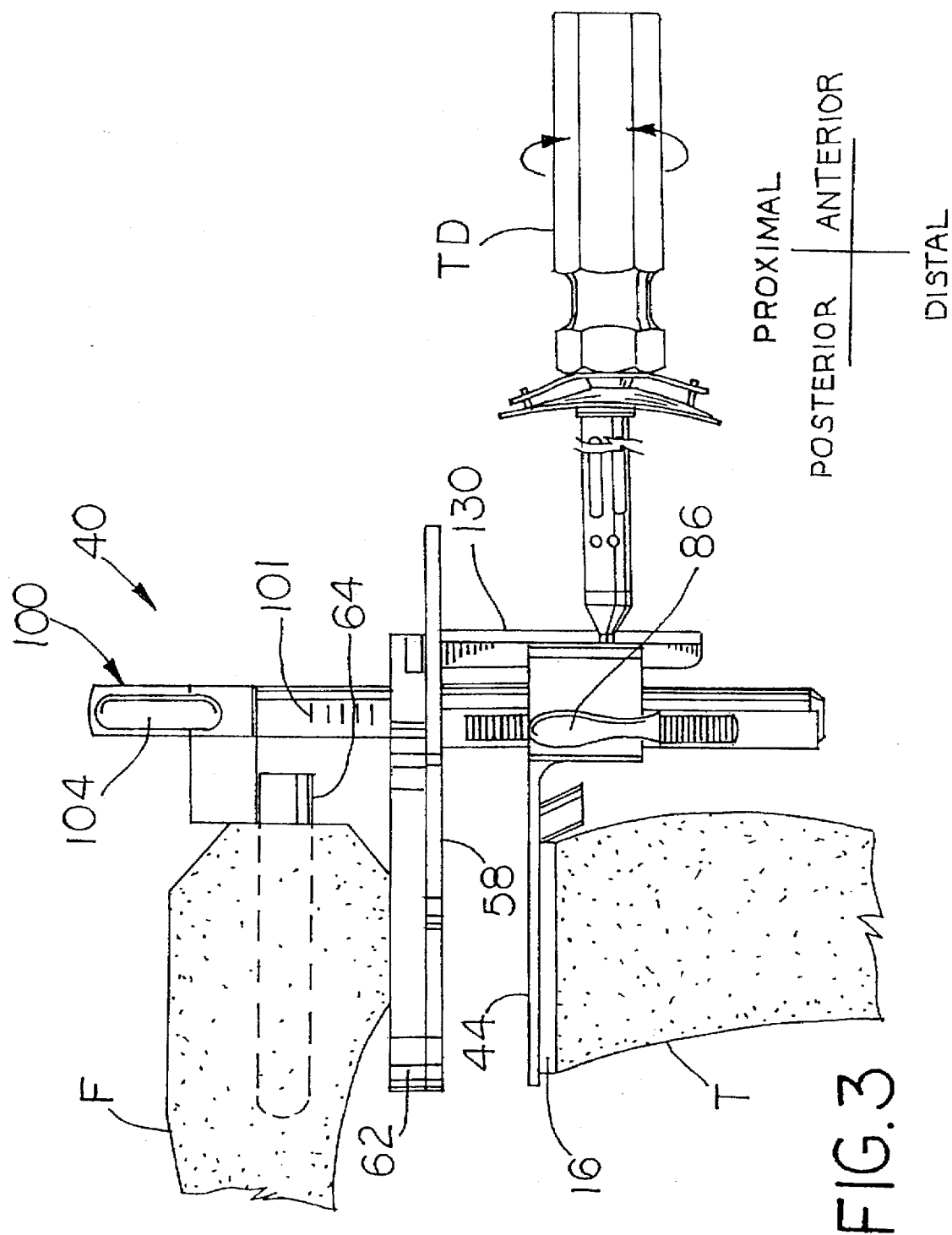
FIG. 3 is a side view of an embodiment of a tensor 40 of the present invention, with the knee joint in a flexion position.

The preferred embodiment herein described is not intended to be exhaustive or to limit the invention to the precise form disclosed. Rather, it is chosen and described to best explain the invention so that others skilled in the art might utilize its teachings.

FIGS. 1–8 illustrate the individual instruments of the instrument set as they would be used in surgery. The figures are generally arranged in a manner such that the instruments are presented in the order that they would be used in an actual revision knee surgery. The description of the invention will therefore begin with a general description of the use of the instruments as illustrated in FIGS. 1–8.

The instrumentation shown in the drawings and described herein is used in a revision knee surgery for replacing existing orthopaedic implants in the distal femur and proximal tibia from a primary surgery with new orthopaedic implants. The distal femur and proximal tibia therefore typically include previously cut and shaped surfaces adapted to mate with corresponding surfaces on the implants used in the primary surgery. Since such surfaces may not be configured to mate with the new implants which are to be used in the revision surgery, or otherwise may be unsuitable for reuse, it is typically necessary to re-cut or reshape one or more of the previously cut surfaces during the revision surgery.

To provide the reader with the proper orientation of the instruments and to assist in more fully understanding the construction of the instruments, a small chart is included on many of the figures. The charts indicate the general directions, i.e., anterior, posterior, medial, and lateral, as well as proximal and distal. These terms relate to the orientation of the femur and will be used in the descriptions of the various instruments consistent with their known medical usage.

Initially, the surgeon, using a known tibial cutting guide (not shown) resects the proximal surface of the tibia, if necessary, to provide a flat surface substantially perpendicular to an anatomical axis of the knee joint. The surgeon then installs a tibial plate 16, which may be a provisional implant, onto the resected proximal tibia. As will be seen below, the plate provides a stable surface for contact by the various instruments of the invention. Alternatively, if the primary tibial plate is still affixed to the tibia and in good condition, the surgeon may choose to leave the tibial component in place.

Figure 5:
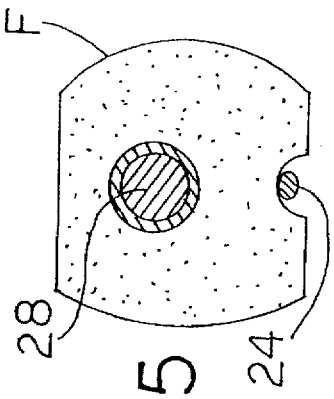
FIG. 5 is a sectional view taken along line 5—5 in FIG. 1.

Referring to FIGS. 1, 2 and 5, the surgeon must establish the rotational alignment of the femur. To do so, the intramedullary (IM) rod 28 of the rotational alignment guide 10 is inserted into the femur F as illustrated in FIGS. 1 and 2. The guide 10 is inserted until the body 12 of guide 10 contacts the distal end of femur F. During insertion of guide 10, the surgeon manually adjusts the position of guide 10 relative to the femur F in an anterior-posterior direction so that a removable pin 24 contacts a notch 32 between the previously resected posterior condyles (PC) as illustrated in FIG. 5. A handle 22 allows the surgeon to move removable pin 24 toward and away from IM rod 28, and apply tension to femur F to check the balance and spacing thereof relative to tibial plate 16. IM rod 28 may be locked into place relative to a tube 20 and body 12 by rotating arms 27 and thereby moving arms 27 in an axial direction against tube 20, as will be described in more detail below. With the instrument properly positioned as illustrated in FIGS. 1 and 2, the posterior surface of body 12 should be approximately parallel to the upper surface of tibial plate 16. This provides a quick visual indication to the surgeon of proper alignment of guide 10. To further verify proper alignment, the surgeon may visually align rotational alignment guide 10 with known anatomical landmarks such as the epicondyles or the anterior femur.

Once the surgeon is satisfied with the alignment of the alignment guide 10, a pin (not shown) is inserted into at least one throughbore 30 of pinning guide 26 on either side of tube 20 and into the distal femur F. With pinning guide 26 thus pinned to femur F, pin 24 is removed and body 12 may be moved anteriorly or posteriorly in sliding relationship to pinning guide 26 while still maintaining a correct angular orientation of guide slots 18. The posterior condyles PC may then be re-cut with a saw blade (not shown) as guided by guide slots 18 in body 12 of rotational alignment guide 10. It is to be understood that each posterior condyle PC need not necessarily be re-cut at the same level as it is the surgeon's goal to leave as much bone as possible during a revision procedure. Fore example, FIGS. 4 and 5 illustrate that the media/posterior condyle has been resected more that the lateral posterior condyle, presumably in response to the amount of defect in the condyles after removal of the primary implant. After the condyles have been resected the appropriate amount, the rotational alignment guide is then removed.

Figure 4A:
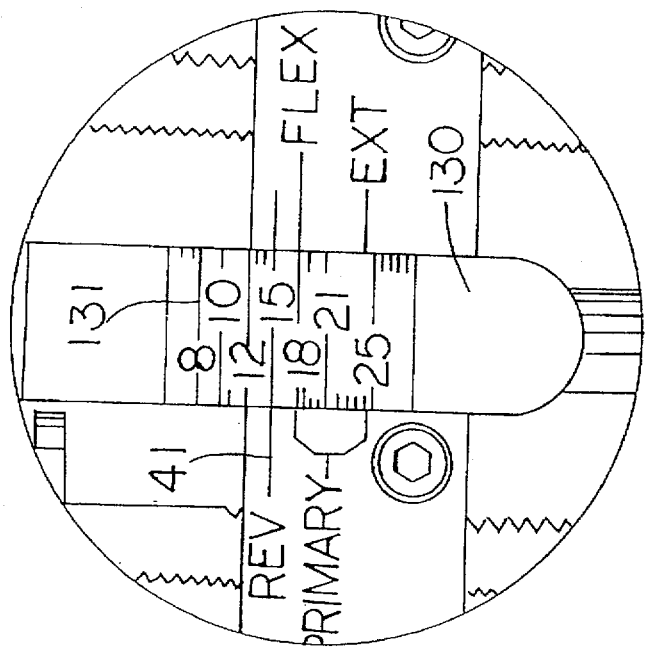
FIG. 4A is an enlarged view of the poly thickness guide shown in FIGS. 3 and 4.
Figure 4:
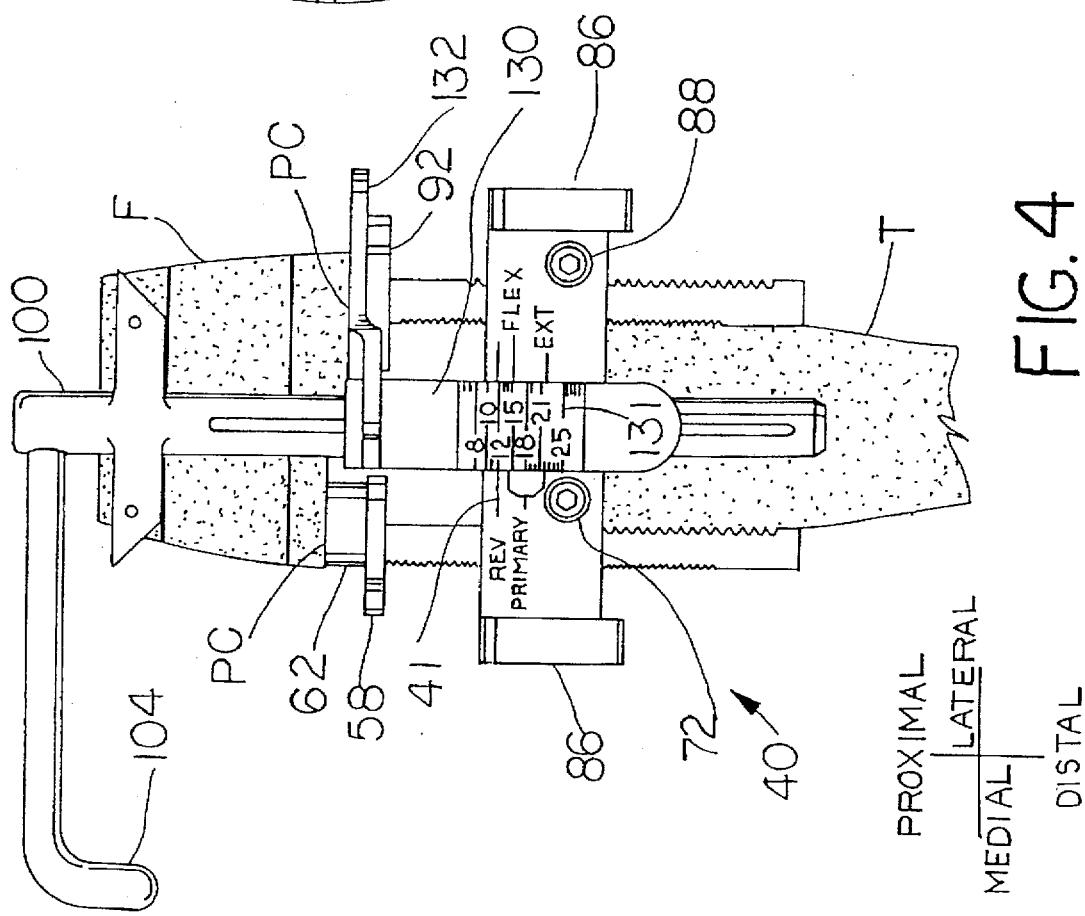
FIG. 4 is an end view of the tensor shown in FIG. 3.

Referring now to FIGS. 3, 4 and 4A, the surgeon next places the flexed knee joint in tension by inserting a tensor 40 between tibia T and femur F. Tensor 40 includes many similarities to the tensor described for use in the primary surgery in the parent application, i.e., U.S. patent application Ser. No. 08/369,226; however, tensor 40 also includes other distinct features and advantages as will become more apparent hereinafter.

Tensor 40 includes a first paddle 44 which contacts the tibial plate 16 and a second set of paddles 58, 92 which contact the resected posterior femoral condyles PC as illustrated in FIGS. 3 and 4. The second set of paddles 58, 92 are connected to independent ratchet drives 72, 88 which extend the distance between the paddles 58, 92, and 44. A torque driver (TD) is used to spread the second set of paddles 58, 92 from the first paddle until a predetermined mount of force is exerted between the femur and the tibia. Tensor 40 includes ratchet pawls for preventing the second set of paddles from inadvertently shifting toward the first paddle 44, and quick release levers 86 for allowing free sliding movement of paddles 58, 92 relative to paddle 44. Tensing the flexed knee joint allows the surgeon to balance and fine tune the soft tissue and select the proper size of femoral component, augment and articular surface thickness as described below. Balancing the soft tissue is accomplished in a variety of known methods such as placing a small incision in one of the ligaments to allow the ligaments to "release" or stretch a small amount. If the soft tissue balance requires a more significant adjustment, the surgeon can opt to readjust the instruments of the invention or may choose to re-cut the tibia or choose to use a constrained prosthetic knee joint.

According to one aspect of the present invention, one or more augments or spacers 62 may be stacked between femur F and a paddle 58 or 92. Augments 62 accommodate the situation where one posterior condyle PC is resected more than the other posterior condyle PC of femur F (FIG. 4) due to the condyle having a larger defect after removal of the primary implant. In the embodiment shown in FIG. 4, paddle 92 is placed directly against the associated posterior condyle PC, while one or more augments 62 are placed between paddle 58 and the other posterior condyle PC such that paddle 58 is substantially coplanar with paddle 92 when an equal and predetermined force is applied to each of paddles 58 and 92 through respective ratchet drives 72, 88.

With the knee flexed and tensed (FIGS. 3 and 4), femur F may be sized in one of two different ways. To wit, femur F may be sized using the distance between paddles 58, 92 and the longitudinal axis of an IM stem extension 64 (FIG. 3), or the distance between paddles 58, 92 and the anterior surface of femur F using a sizer arm 104 (shown in a non-used position in FIGS. 3 and 4). More particularly, sizer guide 100 includes a plurality of indicia 101 thereon relating to the size of the femoral component required for the femur. Indicia 101 may be in the form of letters or numbers corresponding to a particular sizing scheme used by the manufacturer for femoral components. In the particular embodiment shown in FIG. 3, the indicia 101 relates to the distance between the longitudinal axis of IM stem extension 64 and paddle 58. The value of indicia 101 adjacent to paddle 58 is read by the surgeon to provide a proper indication of the correct size of the femoral component. Alternatively, if the anterior surface of the femur is in good shape, femoral sizer 100 may be rotated approximately 90 degrees such that the end of sizer arm 104 contacts the anterior surface of femur F to provide an indication of the distance between the anterior surface of femur F and paddle 58, and thereby provide an indication of the femoral component required for the femur.

A poly thickness guide 130 is slidingly carded by tensor 40 in an overlying relationship to femur sizer 100. Poly thickness guide 130 includes a transverse arm 132 which selectively contacts either of paddle 58 or paddle 92. Poly thickness guide 130 includes a plurality of indicia 131, which relates to the thickness of the poly component required in flexion as well as indirectly indicating the mount of distal femoral bone to be removed. The surgeon determines the thickness of the tibial articulating surface (poly) required by reading the indicia 131 on the poly thickness guide 130 aligned with a hash mark 41 formed on the face of the tensor 40. Referring again to FIG. 4A, the set-up indicates that a 15 mm poly component is required for the patient's knee in flexion.

The embodiment of tensor 40 shown in FIGS. 3, 4 and 4A also includes hash marks designated "FLEX" and "EXT" for measurements to be taken during a primarily surgery in flexion and extension, respectively as explained in parent application. These hash marks are not used by the surgeon during a revision surgery, and in fact may be eliminated if tensor 40 is only used for a revision surgery.

After balancing the knee in flexion as described above, the surgeon then unlocks the tensor 40, places the knee in extension and again tenses the knee in a similar manner as was described above (FIGS. 6–8). With the knee in extension, the arm 104 of the sizer 100 is simply pivoted to a position adjacent the femur and out of the surgeon's way. One or more augments 62 are placed between the distal femur and a paddle 58 or 92 such that paddles 58 and 92 are substantially coplanar with each other, as described above. In the embodiment shown in FIG. 7, a single augment 62 is disposed between the distal end of femur F and paddle 58. An augment with approximately the same thickness will be used in conjunction with the femoral component and allows the distal end of femur F to include two adjacent surfaces which are substantially non-coplanar with each other, thereby allowing as little of the distal end of femur F as necessary to be removed.

Next, the surgeon positions poly thickness guide 130 such that transverse arm 142 engages a selected one of paddles 58 or 92 as described above with reference to FIGS. 4 and 4A. The surgeon reads an indicia 131 aligned with the hash mark 41 on the face of the tensor 40. As illustrated in FIG. 7, the guide 130 indicates a number of 12.

Figure 8:
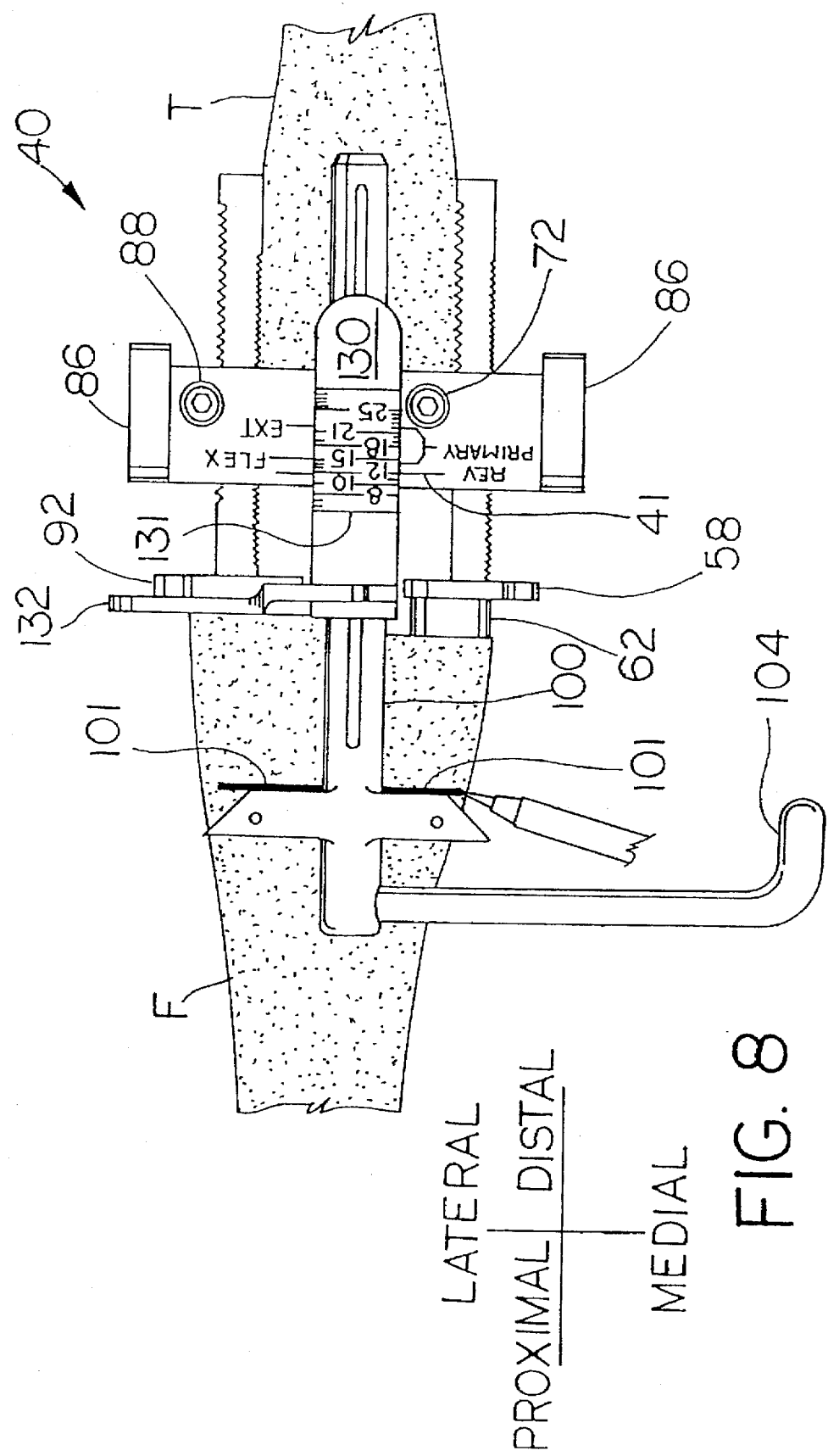
FIG. 8 is another top view of the tensor shown in FIGS. 6 and 7.

Referring to FIG. 8, after the knee joint is properly balanced, sized and aligned, reference lines 101 may be formed on femur F for future reference using sizer guide 100 as a template. An intramedullary alignment guide (not shown) may also be used for setting the valgus angle to a valgus angle determined by the surgeon. Such an alignment guide is described in the parent application (i.e., U.S. patent application Ser. No. 08/369,226) as well as U.S. patent application Ser. No. 08/265,884, each of which are assigned to the assignee of the present invention and incorporated herein by reference. Reference lines 101 may also be used, e.g., to align a provisional implant or to align a cutting or milling guide.

The surgeon subtracts the reading from the extension poly thickness guide 130 taken in extension from the reading obtained from poly thickness guide 130 taken in flexion to determine the mount of bone to be removed relative to a standard resection. Continuing the example illustrated in the figures, the reading in flexion was 15; subtract the reading in extension of 12; leaving a remainder of 3. Therefore, the surgeon deduces that for a proper soft tissue balance and ligament tension for the knee joint, an additional 3 mm of bone should be removed as compared to the standard cut. If the result would have been a negative number, the surgeon would adjust the instruments as explained below to resect 3 mm less relative to the standard cut.

Figure 9:
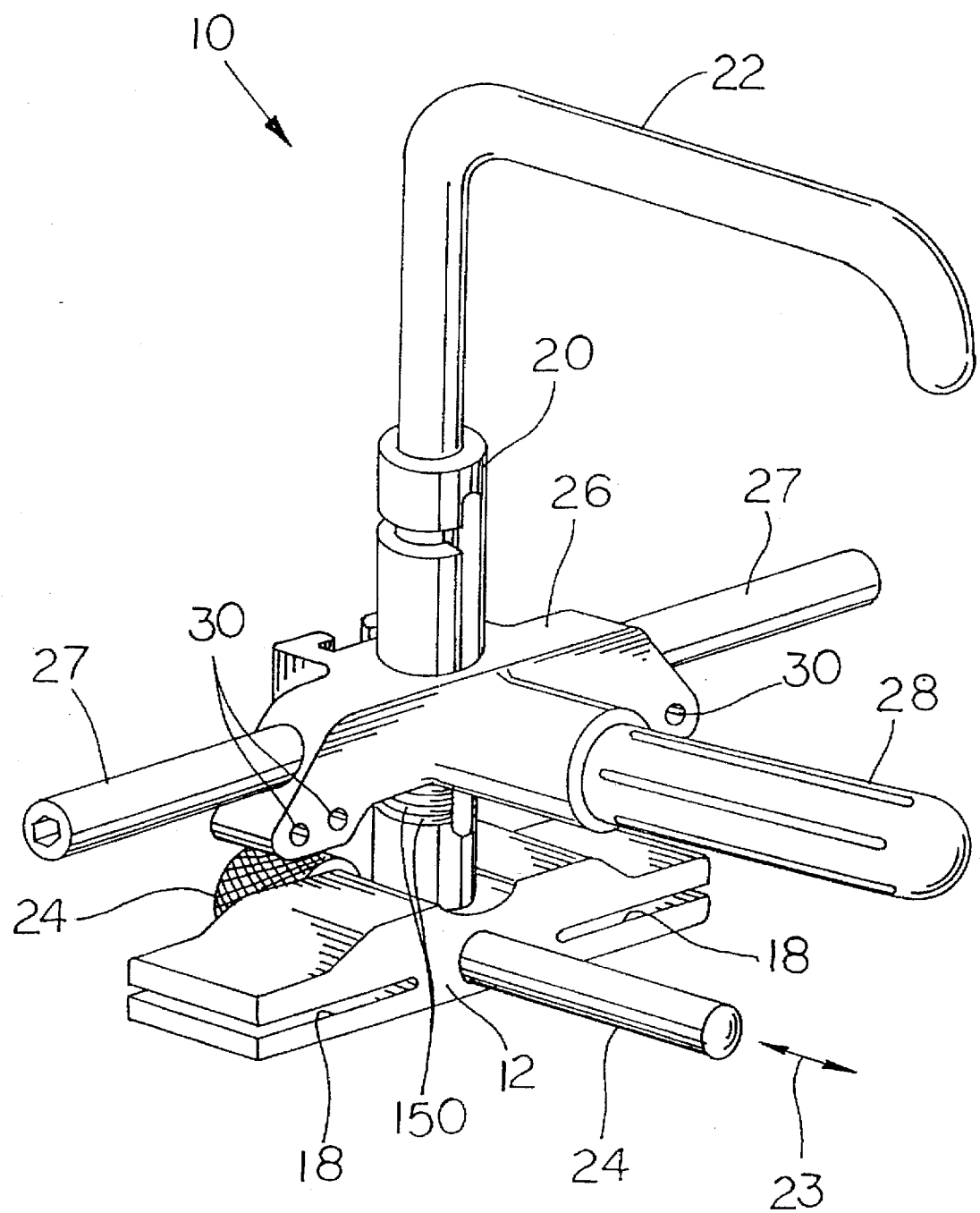
FIG. 9 is a perspective view of the rotational alignment guide shown in FIGS. 1 and 2.

Referring now to FIGS. 9–12, rotational alignment guide 10 is illustrated in greater detail. Rotational alignment guide 10 includes a generally rectangular body 12 having a pair of opposed slots 18 extending therethrough as illustrated best in FIGS. 9 and 10. Guide 10 includes a plurality of through bores 30 therethrough which accommodate pins (not shown) for stabilizing the body 12 during resection of the posterior condyles. A tube 20 extends anteriorly from body 12 and includes a handle 22. Tube 20 includes a plurality of annular grooves or detents 150. A removable pin 24 is removably connected to body 12 and extends proximally from body 12. Removable pin 24 is slidingly connected to body 12, as indicated by double-ended arrow 23 (FIGS. 9 and 11). A pinning guide 26 is shiftably carded by tube 20 and extends substantially parallel to body 12. An IM rod 28 extends proximally from pinning guide 26. As illustrated best in FIGS. 9 and 10, the pinning guide 26 includes two pairs of throughbores 30 positioned on the medial and lateral sides of pinning guide 26 relative to tube 20. Arms 27 extend medially and laterally from pinning guide 26, and lock pinning guide 26 relative to tube 20 and allow the surgeon to visually align guide 10 with known anatomical landmarks.

Figure 12:
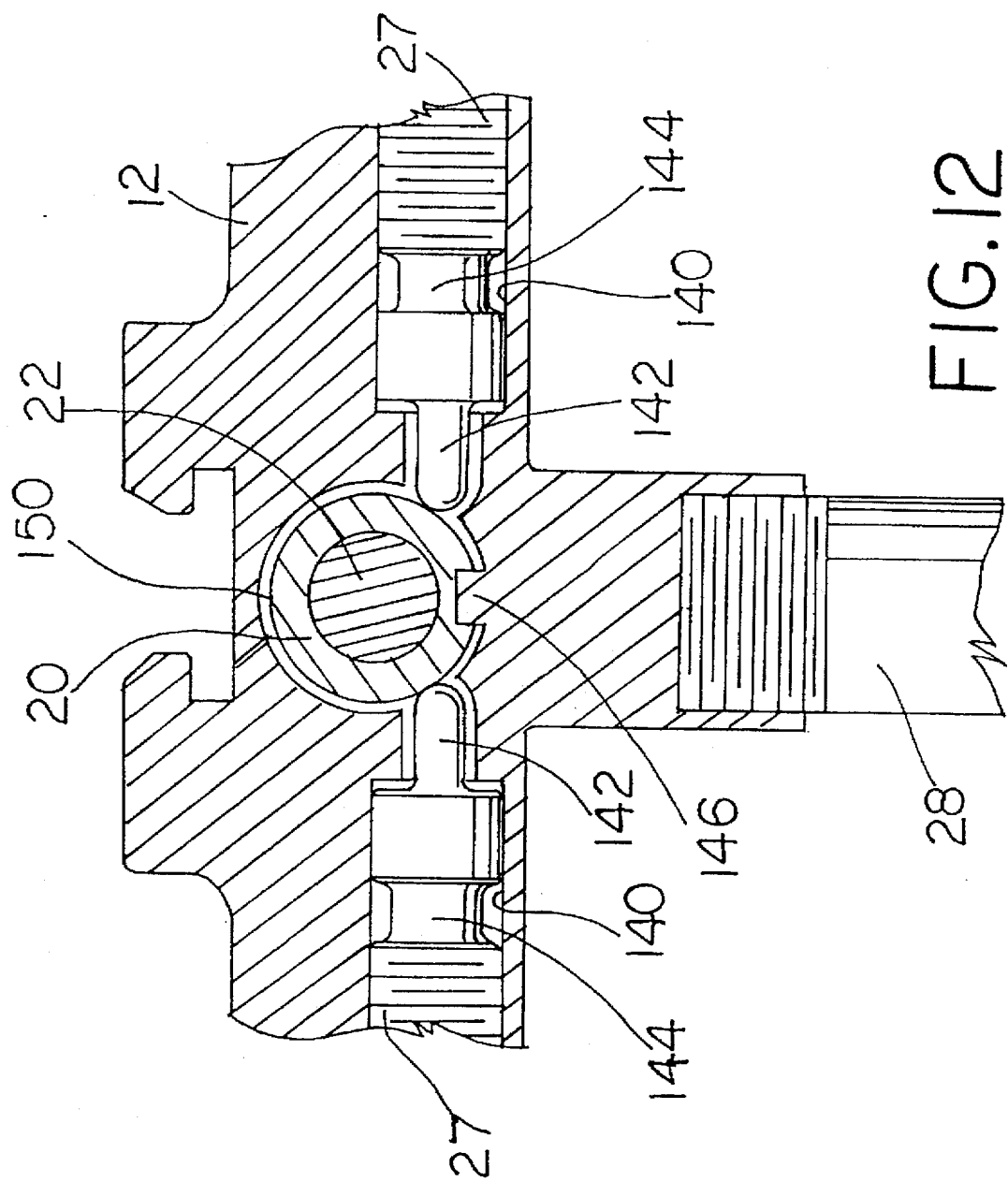
FIG. 12 is a sectional view taken along line 12—12 in FIG. 11.

Referring now to FIG. 12, the locking interrelationship between arms 27 and tube 20 is shown in greater detail. In particular, each arm 27 includes external threads (not numbered) which are threadingly received within a respective opening 140 formed in body 12. The threads on each arm 27, in the embodiment shown, are anti-reversing threads having a slight mismatch in alignment with the corresponding internal threads of the respective opening 140. Each arm 27 includes a tip 142 and a thread relief portion 144. Each tip 142 is disposed offset relative to the longitudinal axis of tube 20 and handle 22. Tips 142 thus exert a radial as well as a tangential force on tube 20 which causes tube 20 to be biased against an opposing wall of the opening (not numbered) within body 12 which is generally opposite from a projection 146. Projection 146 prevents rotational movement of tube 20 within the opening formed in body 12. By placing tips 142 of arms 27 off-set relative to the longitudinal axis of tube 20, tips 142 are deflected slightly in a transverse direction upon axial engagement with tube 20. This slight deflection of tips 142 assists in locking arms 27 relative to body 12 and inhibiting movement between tube 20 and body 12. Tips 142 seat within one of the annular grooves or detents 150 of tube 20.

It should be understood that the invention is not to be limited to the precise form disclosed but may be modified within the keeping of the following claims.

What is claimed is:

1. An orthopaedic instrument for use in orthopaedic surgery, comprising:

a body having a first opening and a second opening, said second opening being in communication with said first opening and extending transverse to said first opening;

a first elongate member being slidingly disposed within said first opening and defining a longitudinal axis; and a second elongate member being threadingly engaged within said second opening, said second elongate member being offset relative to said longitudinal axis of said first elongate member and having a tip configured to engage said first elongate member and apply both a radial and tangential force to said first elongate member, thereby inhibiting movement of said first elongate member within said first opening.

2. The orthopaedic instrument of claim 1, wherein said instrument comprises a rotational alignment guide, and wherein said first elongate member comprises a handle and said second elongate member comprises an arm, said arm being configured to engage said handle and thereby lock said handle relative to said body.

3. The orthopaedic instrument of claim 1, wherein said body includes a third opening being in communication with said first opening and extending transverse to said first opening, and further comprising a third elongate member being disposed within said third opening, said third elongate member being offset relative to said longitudinal axis of said first elongate member and having a tip configured to engage said first elongate member and apply both a radial and tangential force to said first elongate member, thereby inhibiting movement of said first elongate member within said first opening.

4. The orthopaedic instrument of claim 3, wherein said instrument comprises a rotational alignment guide, and wherein said first elongate member comprises a handle and each of said second elongate member and said third elongate member comprise an arm, each said arm being configured to engage said handle and thereby lock said handle relative to said body.

5. The orthopaedic instrument of claim 1 wherein the first elongated member includes a plurality of annular grooves forming detents, said second elongated member being engageable with one of the plurality of annular grooves of the first elongated member.

* * * * *